(12) United States Patent
Davidson et al.

(10) Patent No.: US 8,702,648 B2
(45) Date of Patent: Apr. 22, 2014

(54) CONTROLLED RELEASE MECHANISM FOR BALLOON CATHETERS

(75) Inventors: James F. Davidson, Fladstaff, AZ (US);
Matthew E. Doyle, Newark, DE (US);
Peter R. Giovale, Flagstaff, AZ (US);
David R. King, Wilmington, DE (US);
Paul M. Kroncke, Secane, PA (US);
Alison Keach Pearsall, Wilmington, DE (US)

(73) Assignee: W.L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/209,199

(22) Filed: Aug. 12, 2011

(65) Prior Publication Data

US 2011/0301537 A1    Dec. 8, 2011

Related U.S. Application Data

(62) Division of application No. 11/082,174, filed on Mar. 16, 2005, now Pat. No. 8,021,386.

(51) Int. Cl.
*A61M 29/00* (2006.01)
*A61M 31/00* (2006.01)

(52) U.S. Cl.
USPC ....................... 604/96.01; 604/509

(58) Field of Classification Search
USPC ........ 604/96.01, 101.01, 99.01, 99.02, 99.03, 604/915, 916, 919; 606/193–194
See application file for complete search history.

(56) References Cited

U.S. PATENT DOCUMENTS

| | | | |
|---|---|---|---|
| 3,995,623 A * | 12/1976 | Blake et al. .................... 600/381 |
| 4,813,934 A * | 3/1989 | Engelson et al. .......... 604/99.02 |
| 5,078,681 A | 1/1992 | Kawashima et al. |
| 5,366,442 A | 11/1994 | Wang et al. |
| 5,879,347 A * | 3/1999 | Saadat ............................ 606/28 |
| 6,120,477 A | 9/2000 | Campbell et al. |
| 6,206,852 B1 | 3/2001 | Lee |
| 6,375,637 B1 | 4/2002 | Campbell et al. |
| 6,544,222 B1 | 4/2003 | Yang |
| 6,841,029 B2 | 1/2005 | Lim |
| 7,220,257 B1 * | 5/2007 | Lafontaine ...................... 606/21 |
| 2002/0138081 A1 | 9/2002 | Blaeser et al. |
| 2003/0149339 A1 | 8/2003 | Ishibiki |
| 2004/0116956 A1 | 6/2004 | Duchamp et al. |

FOREIGN PATENT DOCUMENTS

| EP | 1121955 | 8/2001 |
|---|---|---|
| EP | 1504786 | 2/2005 |
| WO | 2004/054651 | 7/2004 |

* cited by examiner

*Primary Examiner* — Manuel Mendez
(74) *Attorney, Agent, or Firm* — David J. Johns (57) ABSTRACT

This invention relates to the field of balloon catheters and more particularly to catheter balloons having controlled failure mechanisms for the prevention of catastrophic failure of the balloon during overpressure conditions.

13 Claims, 6 Drawing Sheets

CONTROLLED RELEASE MECHANISM FOR BALLOON CATHETERS

CROSS-REFERENCE TO RELATED APPLICATIONS

This application is a divisional of co-pending application Ser. No. 11/082,174, filed Mar. 16, 2005 now U.S. Pat. 8,021,386.

FIELD OF THE INVENTION

The present invention relates to the field of balloon catheters and more particularly to catheter balloons having controlled failure mechanisms for the prevention of catastrophic failure of the balloon during overpressure conditions.

BACKGROUND OF THE INVENTION

Balloon catheters are used for a variety of medical procedures, including endovascular treatments. These endovascular treatments are carried out in the lumen of a vascular duct or vessel and have the advantage of being less aggressive and invasive than open surgery. Their conventional use entails the insertion of the balloon catheter into a body conduit at an entrance site and pushing the length of the catheter progressively into the body conduit until the balloon located at the distal end of the balloon catheter reaches the desired site. The balloon is then inflated at that site in order to implement the desired therapy. The body conduit is most often a blood vessel and more particularly an artery, although balloons are used within a variety of other body conduits such as, for example, bile ducts. The inflation of the balloon may be used for various therapeutic reasons. Common uses for balloon catheters include: dilation procedures, occlusion of blood flow, delivery of a pharmaceutical composition to the specific site of inflation, disruption of plaque or thrombus, or to deliver a device to a desired site within the body conduit. Devices most commonly delivered with a catheter balloon include vascular stents and intraluminal vascular grafts both of which may be circumferentially distended by inflation of the balloon until the device is implanted in firm contact with the wall of the blood vessel or conduit.

In use, catheter balloons are known to occasionally rupture due to inflation to higher than designed for pressures. Conventional catheter balloons vent radially in the event of over-pressurization. Sudden rupture and corresponding sudden radial release of inflation pressure fluids or gases has resulted in injury to patients. During a rupture, even if the balloon remains intact, the configuration of the damaged balloon may make withdrawal of the balloon from the body conduit quite difficult. These occasional ruptures can also result in portions of the balloon or emboli being dispersed into the blood vessel or conduit of the patient. Due to displacement of the fragments distally as a result of fluid flow through the blood vessel or conduit, retrieval is difficult and may require interventional surgery. It is further difficult to ascertain with certainty that all pieces have been retrieved. A sudden rupture and release of inflation media due to over-pressurization may also result in damage to the vessel wall requiring additional surgery.

U.S. Pat. No. 5,221,258 to Shturman teaches a catheter balloon having a longitudinal segment of weakness intended to allow the intentional rupture of the balloon between its ends in order to release a device contained within the balloon. Shturman also describes that the balloon may be provided with a portion of larger diameter than the remainder of the balloon in order that the higher hoop stress in the larger diameter portion results in rupture.

U.S. Pat. No. 6,375,637 to Campbell shows a controlled failure balloon mechanism with provision of at least one aperture or slit at least partially through the thickness of the balloon material in at least one end region of the balloon where it is secured to the exterior of the catheter shaft.

None of the prior art balloon catheters provide catheter balloon seals having reliable and controlled failure mechanisms for the prevention of catastrophic failure of the balloon material during overpressure conditions. The present invention provides a balloon catheter with a safe failure design preventing fragmentation of the balloon material in the event of a rupture and further, allowing for safe and easy retrieval of the balloon material from a patient.

SUMMARY OF THE INVENTION

An object of the present invention is to provide a controlled pressure release balloon catheter device which has a predictable and non-catastrophic controlled fail safe mechanism to prevent rupture of the balloon material. The present invention provides a unique balloon catheter device which allows for controlled axial pressure release in the event of an over-pressurized condition. The controlled pressure release balloon catheter is comprised of a catheter shaft having a longitudinal axis extending between a proximal end and a distal end; an inflatable balloon mounted near the catheter shaft distal end and having two ends wherein at least one end of the balloon comprises an angled-cut tail; and a securing band located around at least one end of the balloon comprising the angled-cut tail wherein the securing band holds the balloon in contact with the catheter shaft.

Another object of the present invention is to provide a controlled pressure release catheter device with a varying outer dimension on the catheter shaft and/or balloon which allows for high pressure levels to exist within the balloon during a normal inflation pressure condition in the balloon. The varying outer dimensions on the catheter shaft or balloon also allow for a controlled axial pressure release in the event of excessive pressure within the balloon. The catheter shaft has a longitudinal axis extending between a proximal end and a distal end and has a first outer dimension and a second outer dimension. The inflatable balloon is mounted near the distal end of the catheter shaft with at least one securing band located around at least one end of the balloon. The securing band may be used to hold the balloon in contact with the catheter shaft.

Another object of the present invention is to provide a controlled pressure release catheter with a retainer provided at the end of the catheter shaft spaced apart from the securing band to prevent loss of the securing band in the event of a balloon failure. The device comprises a catheter shaft and inflatable balloon mounted on the catheter shaft via at least one securing band. A retainer is spaced apart from the securing band. In the event of over-pressurization, the retainer has an outer dimension which is greater than or equal to that of the inner dimension of the securing band to impede axial movement and prevent the securing band from breaking free of the catheter device even at excessive pressures.

Another object of the present invention is to provide a controlled pressure release balloon catheter which withstands high inflation pressures and prevents catastrophic balloon rupture due to over-pressurization. The device has an angled-cut tail on the balloon attached via a securing band to a catheter shaft with varying outer dimensions. A retainer is further provided at the distal end of the catheter shaft spaced apart from and distal to the securing band to prevent loss of the securing band in the event of a balloon failure.

Another object of present invention is to provide a controlled axial pressure release catheter wherein the balloon is predictably and safely prevented from material ruptures and fragmentation during over-pressurization by allowing controlled axial pressure release. The substantially axial release of inflation media which occurs upon over-inflation of the balloon in a catheter results in a release of inflation media in a non-perpendicular manner as related to the vessel wall. The pressure release mechanism is not directly opposed to the vessel wall thereby avoiding direct contact with the vessel wall. The benefit of substantial axial release of the inflation media is that the pressure exerted by the inflation media upon exit from the balloon is substantially reduced prior to contact with the vessel wall. This reduced pressure may prevent the occurrence of vessel dissection or rupture. In one embodiment of the present invention the inflation medium is released in a longitudinal direction substantially parallel to the longitudinal axis of the catheter shaft.

BRIEF DESCRIPTION OF THE DRAWINGS

FIGS. 3A through 3D illustrate a sequence for controlled axial pressure release after over-pressurization.

DETAILED DESCRIPTION OF THE INVENTION

Figure 1A:
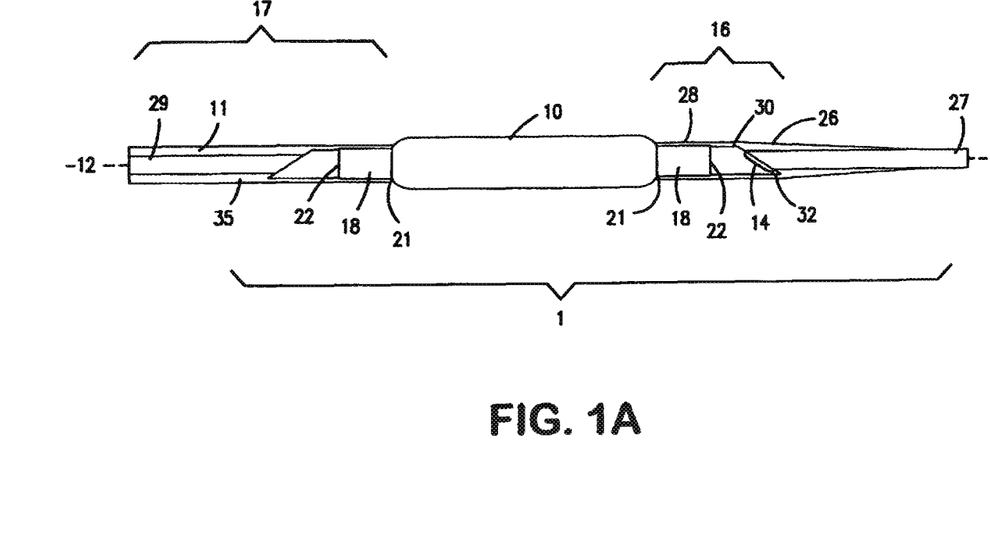
FIG. 1A is a schematic view of the distal end of a controlled pressure release balloon catheter prior to inflation.
Figure 2:
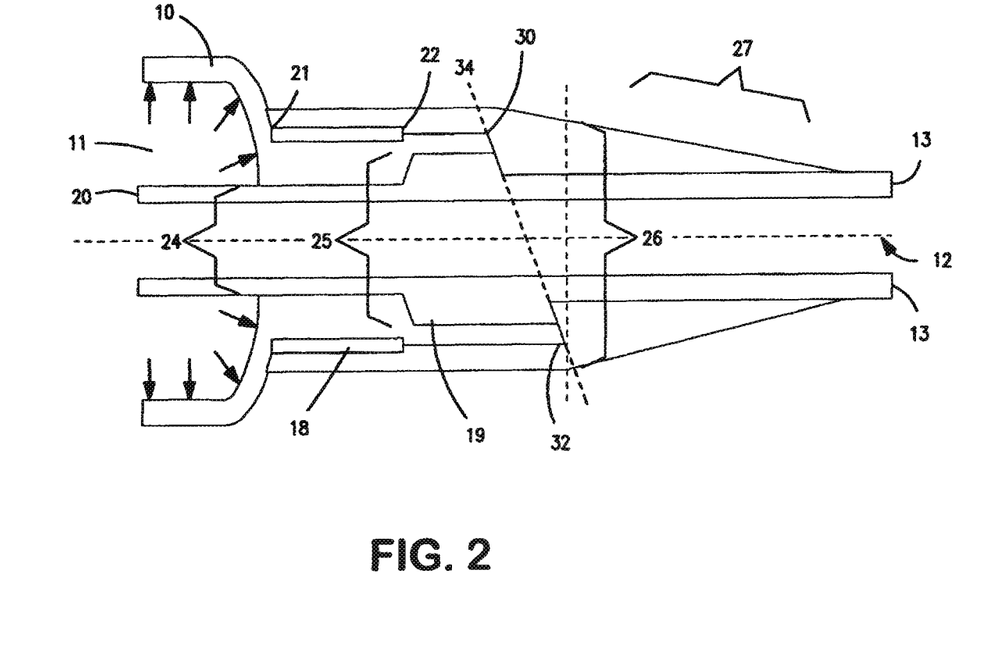
FIG. 2 is a sectioned view of the controlled pressure release balloon catheter near the distal portion of the balloon.
Figure 4A:
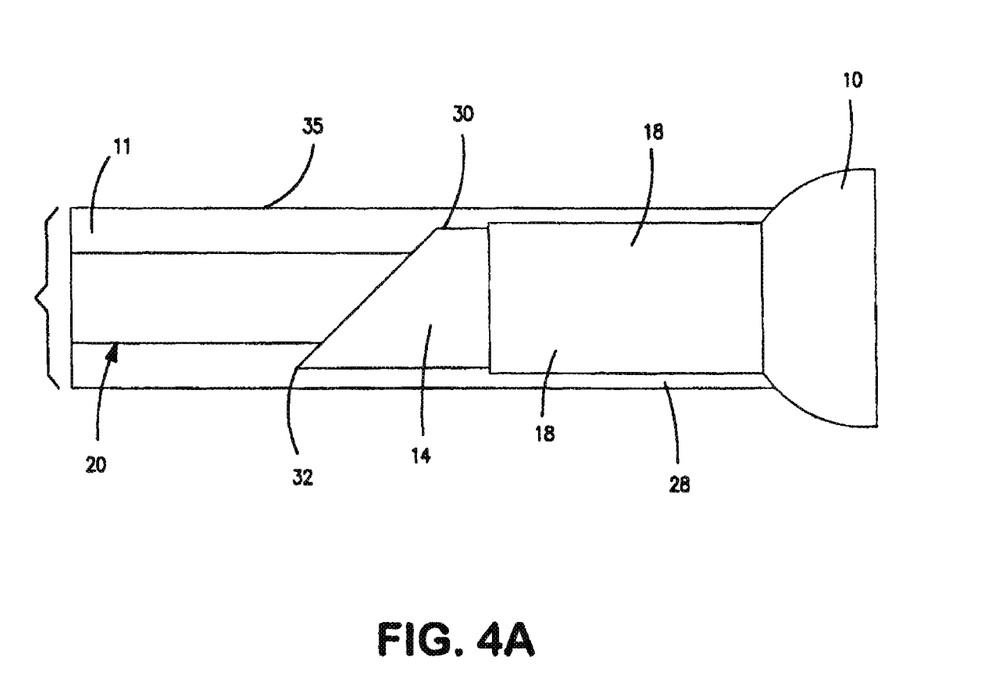
FIG. 4A shows a seal on the proximal end of a balloon catheter.
Figure 4B:
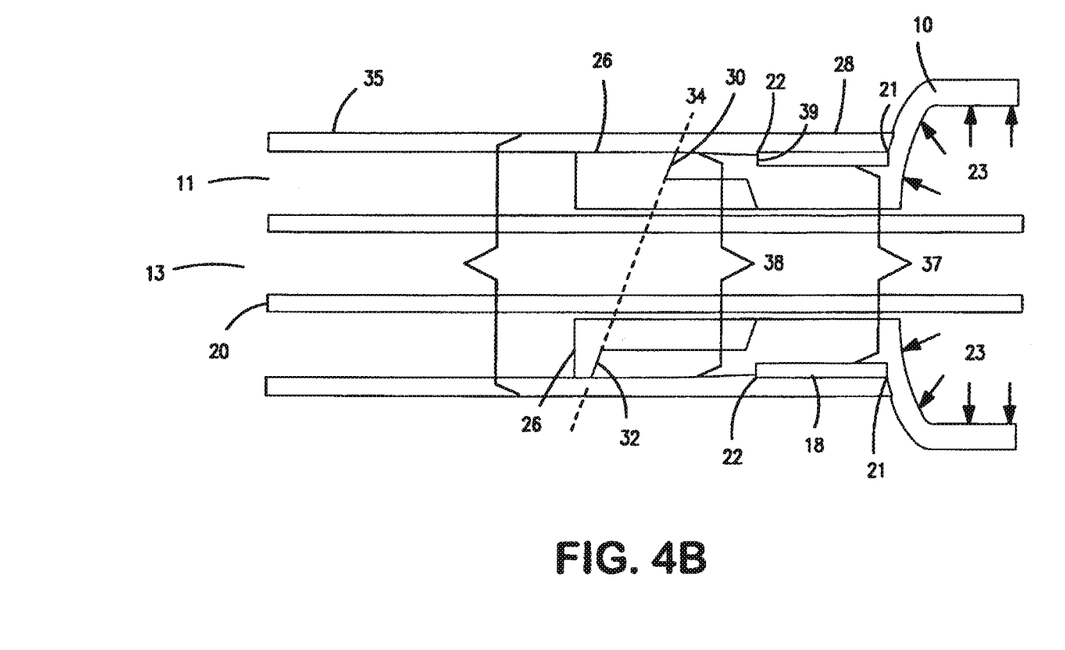
FIG. 4B is a cross-section of a seal on the proximal end of a balloon catheter.

FIG. 1A is a schematic view of a non-inflated controlled pressure release balloon catheter device of the present invention having a controlled failure mechanism in the form of an angled-cut tail present on the balloon. The controlled pressure release catheter device comprises at least a catheter shaft, an inflatable balloon (hereinafter referred to as balloon) with an angled-cut tail, and at least one securing band. The catheter shaft has a longitudinal axis 12 extending between a proximal end 29 and a distal end 27 of the catheter shaft. The balloon has two ends wherein at least one end of the balloon comprises an angled-cut tail. For the purposes of the present invention, the ends of the balloon are those end portions of the balloon that are affixed to a shaft via a securing band 18 and any other portion of the balloon that is on the opposite side of the securing band from the center of balloon 10. The distal end of the balloon 16 is shown mounted or located at the distal end of the catheter shaft 27. The distal end of the balloon 16 constitutes the portion of the balloon 10 that is in closest proximity to the distal-most end of the catheter shaft 27 along with the tail of the balloon protruding from under the securing band 18. FIGS. 1A and 2 show an enlarged view of the distal end of the balloon catheter device. In this embodiment the angled-cut tail is shown as having a short measuring portion 30 and a long measuring portion 32 located adjacent to the securing band 18. The retainer 26 may have a band cover 28 which may be joined to the retainer if desired. The securing band 18 has an inner band edge 21 and an outer band edge 22 and is located around at least one end of the balloon 10 comprising the angled-cut tail 14. The inner band edge 21 of the securing band 18 is that edge which is in closest proximity to the center of the balloon. Likewise, the outer band edge 22 of the securing band is that edge which is opposite the center of the balloon 10. In FIGS. 1A and 2, the securing band 18 holds the balloon 10 in contact with the catheter shaft 20 so that over-pressurization of the balloon 10 allows relative movement between the securing band 18 and the balloon 10 releasing at least a portion of the balloon from the securing band 10 to provide a controlled pressure release mechanism. The securing band 18 is used to secure the distal end 16 of the balloon 10 to the exterior surface of the catheter shaft 20, wherein the proximal catheter shaft end 29 and the distal catheter shaft end 27 may be present on one shaft or may comprise ends of two or more different shafts joined together. A similar binding or securing band 18 may be used to constrain the proximal end 17 of balloon 10 from inflating under normal inflation pressure. The proximal end 17 may or may not be in contact with catheter shaft 20. As shown in FIGS. 4A and 4B, in current embodiment, the proximal end 17 is present on a second catheter shaft 35.

The securing band 18 may comprise any suitable elastomeric or non-elastomeric retaining means. The securing band 18 may further function as a radiopaque marker band. Examples of suitable materials for the securing band 18 include but are not limited to: composite metals, platinum, iridium, stainless steel, titanium, gold, biocompatible metals, polyethylene, polyurethanes, or biocompatible elastomers, thermoplastics, nylon, PEBA, PTFE, or any combination of materials. While the angled-cut tail 14 is shown as a beveled trailing portion of tail present on the end of a catheter mounted balloon 10, it is apparent that an angled-cut tail 14 may be an end of any shape with a short measuring portion 30 and a long measuring portion 32. As shown at FIG. 2, in relation to the distal end of the balloon 16, a short measuring portion 30 has the shortest length of balloon material when measured from the inner band edge 21 of the securing band 18 to the distal most point of the balloon tip. Likewise, the long measuring portion 32 has the longest length of balloon material when measured from the inner band edge 21 of the securing band to the distal most point of the balloon tip. Suitable designs for the balloon tail include: ends with concave designs, notched designs, scallops, stepped designs, triangular cutaways, any other designs with a short measuring portion and a long measuring portion on the balloon tail. The angle associated with the angled-cut tail is measured such that a cross-section of the catheter mounted balloon could reveal two parallel balloon portions of differing lengths, namely the most proximal position on the short measuring portion 30 and the most distal position on the parallel longest measuring portion 32. The same concept may be applied to a securing band comprising a short measuring portion and a long measuring portion coupled with either a blunt-end balloon or a balloon comprising a short measuring portion and a long measuring balloon portion. The parallel measuring portions 30 and 32, are both intersected by a hypothetical third line 34, such as shown in FIG. 2. An interior angle is created between the third line 34 and the parallel balloon portions when viewed in cross section. The angled-cut tail 14 is shown located at the end of the balloon 10. FIGS. 1A and 2 show an optional band cover 28 adjacent to the retainer 26. The retainer 26 may be rounded or tapered on the distal end to facilitate entry or insertion of the balloon catheter into a body conduit. The band cover may be made from a variety of materials well known in the art including PTFE, PET (polyethylene terephthalate), PE (polyethylene), an amide-based thermoplastic elastomer, a polyether block amide (PEBA), such as PEBAX™ (Arkema Chemicals), polyurethanes, polyamides, nylons and biocompatible composite materials suited for use as a band cover. The angled-cut tail 14, while shown by FIGS. 1A and 2 only at the distal end 16 of the balloon 10, may be alternatively located at the proximal end or at both ends of the balloon.

The catheter shaft 20 is shown with corresponding longitudinal axis 12 and a lumen or channel extending throughout the length of the catheter shaft. The catheter shaft 20 may be made from a variety of materials well known in the art including PTFE, PET (polyethylene terephthalate), PE (polyethylene), an amide-based thermoplastic elastomer, polyether block amide (PEBA), such as PEBAX™ (Arkema Chemicals), polyurethanes, polyamides, nylons, biocompatible composite materials, metals or other suitable composites. The catheter shaft is generally a tubular construction and contains at least one passageway or lumen extending between the distal and proximal ends of the catheter device that allows for passage of an inflating medium such as a saline fluid.

The catheter shaft will most generally contain at least one additional passageway that allows for passage of a guidewire device or other element.

The balloon 10 may be virtually any type of known catheter balloon including but not limited to: balloons made from materials such as latex, silicone, polyurethane, biocompatible elastomers, thermoplastics, PTFE, PET (polyethylene terephthalate), or PE (polyethylene). The balloon may also be a composite balloon such as the balloon made as taught by U.S. Pat. Nos. 5,752,934 and 5,868,704 to Campbell et al. For the purposes of this patent the balloon may be uni-body designed or may comprise multiple components, such as reinforced or coated composites.

The securing bands on the distal and proximal ends may be of various forms and materials. For instance, various elastomeric materials or various non-elastomeric materials may be used in the securing bands. The securing band 18 may exist in forms including but not limited to: wrapped narrow strips of film or wire about the ends of the balloon, single or multiple-pieced metal bands, single or multiple-pieced composite bands, interlocking pieces forming a band, or any other suitable securing band design. The proximal and distal securing bands may be alike or different, depending upon desired application. The dimensions and geometric design of the securing band may also vary depending upon the desired application to incorporate features in the bands such as a tapered end on the band, a concentric band, a flared end on the band, or other desired designs. The securing band 18 may or may not be secured by an adhesive to hold the exterior surface of the balloon in contact with the securing band.

FIG. 2 is a sectioned view of the controlled pressure release balloon catheter near the distal portion of the balloon. In this embodiment the controlled pressure release catheter device comprises a catheter shaft 20, an inflatable balloon 10, and a securing band 18. The inflatable balloon 10 may comprise unfolding balloons as well as expansion balloons or any other suitable balloon or device forms. The catheter shaft 20 has a longitudinal axis 12 extending between its proximal end 29 (not shown) of the catheter shaft 20 and the distal end 27 with a second lumen 13 extending therebetween. The catheter shaft 20 further comprises a first outer dimension of the catheter shaft 24 and a second outer dimension of the catheter shaft 25. The un-inflated balloon is mounted on the first outer dimension of the catheter shaft 24 using securing bands. While the balloon in this embodiment is depicted as having an angled-cut tail, a blunt cut tail or any other tail configuration may optionally be used. The balloon 10 is located near the catheter shaft distal end 27 and has two ends. The securing band 18 shown in this drawing is located around at least one end of the balloon 10 to hold the balloon 10 in contact with the first outer dimension of the catheter shaft 24. The second outer dimension of the catheter shaft 25 is located distal to the securing band 18 and is a different diameter than the first outer dimension of the catheter shaft 24. The second outer dimension of the catheter shaft and balloon provides resistance to axial movement of the securing band upon pressurization of the balloon when the diameter is equal or greater than the first outer dimension, thereby providing for the use of a high-pressure balloon. Over-pressurization of the balloon causes relative movement between the securing band and the balloon so that the balloon is released from the securing band to provide a controlled pressure release mechanism. Over-pressurization occurs when a predetermined safe inflation pressure is exceeded thereby risking a failure or rupture of the balloon 10. The predetermined safe inflation pressure is not required to be one specific inflation pressure but may be a range of normal operating pressures. Exceeding a predetermined safe inflation pressure range occurs with pressures extending anywhere between the normal maximum operating pressure and the burst pressure. The burst pressure is obtained when inflating medium 23 is vented due to over-pressurization. FIG. 2 shows an optional band cover 28 on the distal end of the catheter shaft 27. A distal end of the catheter shaft is considered to be the portion of the catheter from the midsection to the furthest most distal end. This embodiment shows varying outer dimensions as related to the catheter shaft, which prevent relative movement between the securing band and the balloon.

In another aspect of this invention, the catheter shaft 20 may comprise a single outer diameter dimension and the balloon may comprise varying outer dimensions. In this regard, the balloon would comprise a first balloon outer diameter dimension and a second balloon outer diameter dimension located distal to the securing band and exhibiting a different outer diameter measurement than the first balloon outer diameter. Thus, the balloon may comprise varying outer dimensions, which prevent relative movement between the securing band and the balloon end, with or without any variation in the catheter shaft outer dimensions.

Figure 3A:
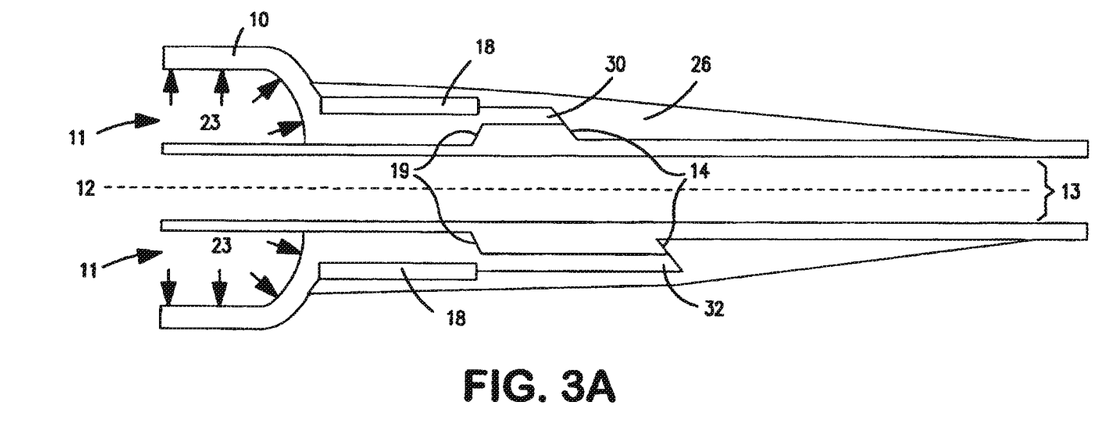
FIG. 3A shows a controlled pressure release balloon catheter in an inflated state.

FIG. 3A is a longitudinal cross section of an inflated controlled release balloon catheter device. In this embodiment the balloon is depicted as having an angled-cut tail 14, however, a blunt cut tail or any other tail configuration may optionally be used. The balloon is inflated via an inflation port intended to be representative of various known inflation medium 23 for conveying into balloon 10 any pressurizing medium such as a saline liquid conveyed to port via a connecting channel or lumen 11. The controlled pressure release catheter device is shown comprising a catheter shaft having a longitudinal axis 12 extending between a proximal end and a distal end and a second lumen 13 extending therebetween. The inflatable balloon 10 has two ends mounted at the catheter shaft distal end, with a securing band 18 located around at least one end of the balloon 10. The securing band 18 holds the balloon 10 in contact with the catheter shaft 20. The catheter shaft may extend through the balloon, but it is not required. A retainer 26 is provided spaced apart from and distal to the outer band edge 22. Over-pressurization of the balloon causes relative movement between the securing band 18 and the balloon 10 so that a portion of the balloon 10 is released from the securing band 18 to provide a controlled pressure release mechanism. The retainer 26 prevents uncontrolled axial release of the securing band 18 from the catheter shaft 20. The retainer 26 may comprise an elastomeric, non-elastomeric or thermoplastic member or any suitable material. In certain embodiments as shown here, the retainer 26 may be joined with band cover 28. The retainer may be round, conical or any other suitable shape and may be joined or extended to include a band cover 28 which encases the securing band 18 and/or the angled-cut tail 14 end of the balloon. The retainer is distinguished as having a diameter sufficient to impede marker band movement. In certain embodiments the retainer has an equal or larger outer diameter measurement than the inner diameter measurement of the securing band. The retainer is located adjacent to the end of balloon 10 and spaced apart from the most distal part of the securing band 18. The retainer preferably co-axially encloses the catheter shaft 20, however the retainer may be configured as a non-coaxial element. Over-pressurization of the balloon causes relative movement between the securing band and the balloon so that the short measuring portion of the balloon is released from the securing band to provide a controlled pressure release mechanism. The release of the short measuring portion of the balloon 30 from the securing band may occur due to pressurized movement of the balloon out from under the securing band, or due to longitudinal movement of the securing band over the balloon.

Figure 3B:
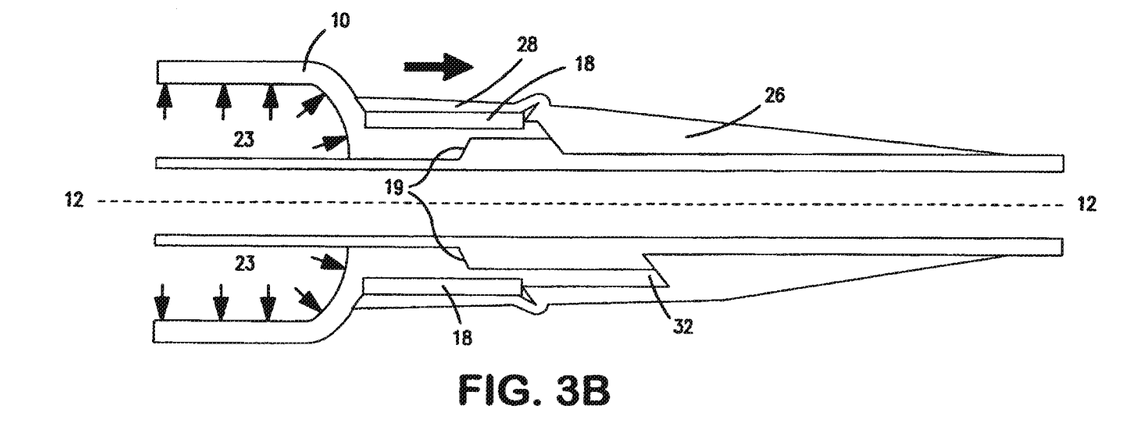
FIG. 3B shows a controlled pressure release balloon catheter at pressure exceeding a predetermined safe inflation pressure, thus initiating axial movement of the securing band.

During an overpressure condition, it is anticipated that the force exerted from the balloon on the securing band 18 will increase until failure commences causing relative movement between the securing band 18 and the balloon tail 14. In one embodiment, the second outer dimension of the catheter shaft will prevent movement of the securing band until such time as the extreme pressure of the balloon forces the securing band to transition over the catheter shaft dimension change 19 and onto the second outer dimension of the catheter shaft, as shown in FIG. 3B. The catheter shaft dimension change 19 is a transitional area which links the first outer dimension of the catheter shaft to the second outer dimension of the catheter shaft. The movement of the securing band continues until the short measuring portion of the angled-cut balloon tail 14 is exposed from its previous location beneath the securing band 18. Once the short measuring portion is free from the securing band, a longitudinal pressure release occurs due to inflation medium contained within the balloon 10 being released through the axial opening 15. Substantially axial pressure release can thus be designed to occur so that the inflation media is directed away from the wall of the vessel. Substantially axial pressure release of inflation media is defined as occurring upon over-inflation of the balloon catheter resulting in a release of inflation media in a manner which directs the media in a non-perpendicular manner as related to the vessel wall. The pressure release mechanism is not directly opposed to the vessel wall thereby avoiding direct contact with the vessel wall. The benefit of substantial axial release of the inflation medium is that the pressure exerted by the inflation media upon exit from the balloon is substantially reduced prior to contact with the vessel wall. The reduced pressure prevents the occurrence of vessel dissection or rupture. In one embodiment of the present invention the inflation medium is released in a longitudinal direction substantially parallel to the catheter shaft.

In another aspect of the present invention, the securing band 18 maintains hold of the longest measuring portion of the angled-cut tail to prevent disassociation of the balloon from the catheter shaft. The securing band is prevented from uncontrolled axial release from the catheter shaft by the retainer 26. The balloon material thus, remains intact and attached to the catheter shaft via the securing band and is able to be easily withdrawn from within the body conduit.

Figure 3C:
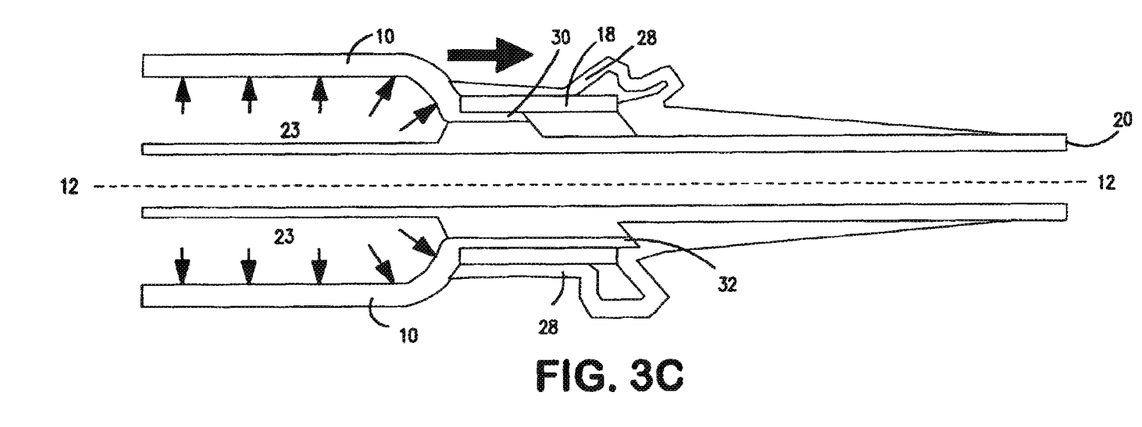
FIG. 3C shows a controlled pressure release balloon catheter at a pressure exceeding a predetermined safe inflation pressure, wherein the securing band movement is axially impeded.
Figure 3D:
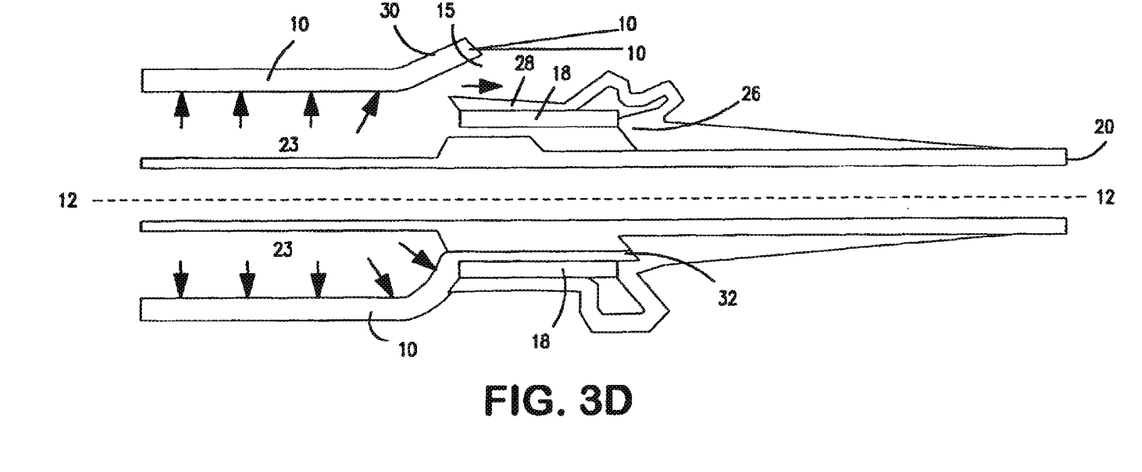
FIG. 3D shows a controlled pressure release balloon catheter in an over-pressurized state venting pressure through an axial opening.

In one preferred embodiment, the controlled pressure release catheter device comprises a catheter shaft 20 having a longitudinal axis 12 extending between a proximal end 17 and a distal end 16 wherein the catheter shaft 20 comprises a first outer dimension 24 and a second outer dimension 25; an inflatable balloon 10 comprised of ePTFE is mounted near the catheter shaft distal end 27. The inflatable balloon 10 has two ends wherein at least one end of the balloon comprises an angled-cut tail 14; a securing band 18 comprising a metal composite, such as platinum and iridium is located around at least one end of the balloon comprising an angled-cut tail. The securing band holds the balloon in contact with the first outer dimension of the catheter shaft. A second outer dimension of the catheter shaft is located distal to the securing band and is greater than the first outer dimension, thereby providing resistance to axial movement of the securing band upon pressurization of the balloon. A retainer is provided at the distal end of the balloon and is spaced distal to and apart from the securing band 18. The retainer is joined to a band cover, to form a single unit which co-axially encases the distal end of the balloon, the catheter shaft dimension change 19 and the securing band 18 when the balloon is in a non-inflated state. In this embodiment the band cover and the retainer 26 are comprised of a polyether block amide, namely a plasticizer free thermoplastic elastomer, such as PEBAX™ (Arkema Chemicals), as shown in FIGS. 3C and 3D. As the balloon reaches a predetermined failure pressure, the balloon begins to exert the necessary force against the securing band 18 to cause relative movement between the securing band 18 and the balloon 10 resulting in at least a portion of the balloon 10 being released from the securing band 18. Once a portion of the balloon is released from the securing band 18 to form the axial opening 15 on the balloon, a pressure release occurs axially to safely vent in the path of the conduit or vessel, and prevent vessel rupture. The balloon 10 remains intact and at least a portion of the balloon 10 continues to be held to the catheter shaft by the securing band. The retainer prevents uncontrolled axial release of the securing band from the catheter shaft as shown in FIG. 3C.

The size of the securing band and the proximity of securing band to the distal end 16 of the inflated balloon 10 will be dependent upon desired applications. The balloon design including the balloon type, angle of cut on the balloon tail, balloon material and the varying outer dimensions of a balloon will need to be engineered for desired applications. Similarly, the catheter shaft material, catheter shaft dimensions, and the first outer dimension and second outer dimension of the catheter shaft will be designed for their desired application.

FIGS. 4A and 4B show seals on the proximal end of a balloon 10 mounted on the distal end of the catheter shaft 20. The securing band 18, the retainer 26, and the band cover 28 in FIG. 4A are shown mounted to a second catheter shaft 35. The second catheter shaft 35 and the first catheter shaft 20 enclose the inflation lumen 11. The inner dimension of the first catheter shaft 20 provides the second lumen 13, as shown in FIG. 4B. Alternatively, multiple lumens may exist within one catheter shaft.

In this embodiment, the proximal catheter shaft end 29 and the distal catheter shaft end comprise ends of different shafts. An angled-cut tail 14 is shown having a short measuring portion 30 and a long measuring portion 32. In FIG. 4B the balloon dimension change 39 is shown as adjacent to a second catheter shaft 35 with the transition from the first outer balloon dimension 37 to the second outer balloon dimension 38.

A guide wire lumen 13 extends throughout a portion or all of the balloon 10. The space in inflation lumen 11 is pressurized with inflation medium so that expansion or unfolding of the balloon 10 occurs. Pressure from the inflation medium 23 causes relative movement between the securing band 18 and the balloon 10. In this FIG. 4B an angled-cut tail 14 is shown, however, any tail shape could be substituted as desired.

In order to ensure that failure begins at a particular end, if that is desired, for example at a securing band 18 on the distal end rather than at the proximal end, the securing band on the proximal end should be made to provide greater resistance to relative movement between the securing band and balloon tail than the distal securing band. This may be accomplished by various methods including the use of a wider or thicker material for the proximal securing band. This may alternatively be accomplished through the use of a longer or non-angled balloon tail on the preferred non-failing end. Generally, any desired method may be used which provides for greater resistance to translation of the securing band at one end than the other, allowing the weaker end to fail at a predetermined inflation pressure.

While the principles of the invention have been made clear in the illustrative embodiments set forth herein, it will be obvious to those skilled in the art to make various modifications to the structure, arrangement, proportion, elements, materials and components used in the practice of the invention. For example, the FIGS. 1A-3D depict a difference between the first outer dimension of the catheter shaft and the second outer dimension of the catheter shaft which allow for a controlled axial pressure release in the event of excessive pressure within the balloon. It would be within the skill of one in the art to create a catheter shaft with a constant outer dimension used with a balloon having a varying outer first and second dimension to provide the same benefits. In these variations, the balloon comprises a longitudinal axis extending between a proximal balloon end and a distal balloon end. The balloon first outer dimension is larger than the distally located balloon second outer dimension. The inflatable balloon is mounted near the distal end of the catheter shaft with a securing band located around at least one end of the balloon to hold the balloon in contact with the constant outer dimension of the catheter shaft. During an overpressure condition, it is the force exerted from the balloon on the securing band 18 which will increase until failure commences causing the securing band 18 to move axially from the balloon first outer dimension toward the balloon second outer dimension. To the extent that these various modifications do not depart from the spirit and scope of the appended claims, they are intended to be encompassed therein.

What is claimed is:

1. A method for axial release of inflation medium in a controlled pressure release balloon catheter device at an intravascular site, comprising the steps of:
   introducing the controlled pressure release balloon catheter device into a vasculature, wherein said catheter has a longitudinal axis;
   advancing the controlled pressure release balloon catheter device through the vasculature to the intravascular site, wherein said controlled pressure balloon has a longitudinal axis;
   expanding said balloon against the vessel wall;
   wherein in the event of excess pressure, releasing inflation medium substantially longitudinally through an angle-cut tail of said balloon.

2. The method of claim 1, wherein a securing band is located around at least one end of said balloon.

3. The method of claim 2, wherein said second catheter shaft outer dimension is greater than the first catheter shaft outer dimension.

4. The method of claim 2, wherein the securing band is located on the first catheter shaft outer dimension prior to balloon inflation.

5. The method of claim 4, wherein the second balloon outer dimension is greater than the first balloon outer dimension.

6. The method of claim 1, wherein said catheter comprises a first catheter shaft outer dimension and a second catheter shaft outer dimension.

7. The method of claim 1, wherein said inflatable balloon comprises a first balloon outer dimension and a second balloon outer dimension.

8. The method of claim 7, wherein the securing band is located on the first balloon outer dimension prior to balloon inflation.

9. The method of claim 8, wherein the band cover is a thermoplastic.

10. The method of claim 8, wherein the band cover is an elastomer.

11. The method of claim 8, wherein a retainer is joined to the band cover on the distal end of the catheter.

12. The method of claim 1, further comprising a band cover.

13. The method of claim 12, wherein the thermoplastic is a polyether block amide.

* * * * *